(12) United States Patent
Berwe et al.

(10) Patent No.: US 6,294,673 B1
(45) Date of Patent: Sep. 25, 2001

(54) PROCESS FOR PREPARING NIFEDIPINE

(75) Inventors: Mathias Berwe, Sprockhövel; Herbert Diehl, Leverkusen; Karl Rittner; Karl-Heinz Wahl, both of Odenthal; Hans-Peter Wirges, Krefeld, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/446,478

(22) PCT Filed: Jun. 15, 1998

(86) PCT No.: PCT/EP98/03591
§ 371 Date: Apr. 26, 2000
§ 102(e) Date: Apr. 26, 2000

(87) PCT Pub. No.: WO99/00369
PCT Pub. Date: Jan. 7, 1999

(30) Foreign Application Priority Data

Jun. 27, 1997 (DE) .............................................. 197 27 350

(51) Int. Cl.[7] ........................ C07D 211/04; C07D 211/08
(52) U.S. Cl. ............................................ 546/249; 546/321
(58) Field of Search ...................................... 546/249, 321

(56) References Cited

U.S. PATENT DOCUMENTS

| 3,485,847 | 12/1969 | Bossert et al. | 260/295.5 |
|---|---|---|---|
| 4,600,778 | * 7/1986 | Teller et al. | 546/249 |
| 5,126,457 | * 6/1992 | Teller et al. | 546/249 |
| 5,723,618 | * 3/1998 | Leung-Toung et al. | 546/121 |
| 5,808,084 | * 9/1998 | Arguelles | 546/249 |

FOREIGN PATENT DOCUMENTS

| 294392 | 2/1991 | (DE) | C07D/211/90 |
|---|---|---|---|
| 290878A | 6/1991 | (DE) . | |
| 4423445 | 1/1996 | (DE) | C07D/211/90 |
| 0124742 | 11/1984 | (EP) | C07D/211/90 |
| 8600745 | 11/1984 | (ES) | C07D/211/90 |
| 2057122 | 3/1996 | (RU) | C07D/211/90 |

OTHER PUBLICATIONS

Watanabe, Y.; Shiota, K.; Hoshiko, T.; and Ozaki, S., "An Efficient Procedure for the Hantzsch Dihydropyridine Synthesis", Synthesis, p. 761 (Sep. 1983).

* cited by examiner

Primary Examiner—Alan L. Rotman
Assistant Examiner—Rita Desai
(74) Attorney, Agent, or Firm—Jerrie L. Chiu

(57) ABSTRACT

The invention relates to a process for the preparation of nifedipine by the reaction of methyl 2-(2-nitrobenzylidene) acetoacetate and methyl 3-aminocrotonate and the use of the nifedipine thus prepared for the production of a medicament.

6 Claims, No Drawings

PROCESS FOR PREPARING NIFEDIPINE

CROSS-REFERENCE

This application is a 371 of PCT/EP98/03591 filed Jun. 15, 1998.

The invention relates to a new process for the preparation of nifedipine.

The compound dimethyl 1,4-dihydro-2,6-dimethyl-4-(2-nitrophenyl)-3,5-pyridinedicarboxylate of the formula:

nifedipine (I)

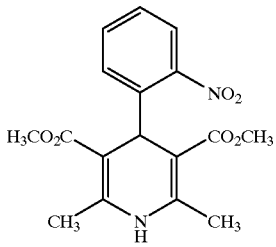

is known as the pharmaceutical active compound nifedipine (U.S. Pat. No. 3,485,847).

Nifedipine is a recognized pharmaceutical active compound which is used worldwide in large amounts medicinally. For such pharmaceutical active compounds, there is a particular interest in an economical preparation process which produces the active compound in high purity and good yields.

U.S. Pat. No. 3,485,847 describes its preparation from methyl acetoacetate, 2-nitro-benzaldehyde and ammonia. A yield of about 72% of theory is achieved here.

The nifedipine obtained by this process, however, does not have the purity which is demanded for use as a pharmaceutical active compound.

Thus DD 294 392 and DD 290 878 describe special purification processes for (I) which for the first time make possible use as a pharmaceutical active compound.

Such purification operations are associated with yield losses, such that the yields of pure nifedipine are significantly below those of the synthesis processes.

In view of the disadvantages of the process of U.S. Pat. No. 3,485,847, the inventors of DE-A-33 12 216 (EP-A-0 124 742) set themselves the task of making available an improved process for the preparation of the 1,4-dihydropyridines in which these are obtained in higher purity. To this end, DE-A-33 12 216 discloses a process for the preparation of nifedipine by reaction of methyl 2-(2-nitrobenzylidene)acetoacetate and methyl 3-aminocrotonate in which the starting substance methyl 2-(2-nitrobenzylidene)acetoacetate is prepared by a specific catalytic process. The reaction of the methyl 2-(2-nitrobenzylidene)acetoacetate with the methyl 3-aminocrotonate is carried out in methanol under reflux (about 65° C.) in the example. To achieve a high yield, very long reaction times are needed according to this process. Thus the benzylidene compound and the aminocrotonic acid ester are heated under reflux for 36 hours. In this case, yields of about 80 to 87% of theory are obtained. The (I) obtained according to DE-A-33 12 216, however, still does not show the purity which is demanded for use as a pharmaceutical active compound. Thus by means of HPLC analysis the presence of the valence isomer (II) in the per cent range can be detected, whose removal/rearrangement makes an additional pure crystallization necessary. The yield is then only 70–75% of theory.

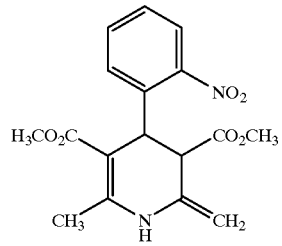

(II)

DE-A-44 23 445 was based on the object of overcoming the disadvantages of DE-A-33 12 216 (EP-A-0 124 742) described above. DE-A-44 23 445 describes a process for the preparation of nifedipine by reaction of methyl 2-(2-nitrobenzylidene)acetoacetate and methyl 3-aminocrotonate in methanol as solvent at temperatures between 40 and 100° C., characterized in that the reaction is carried out in the presence of catalytic amounts of a lower carboxylic acid. In the examples of DE-A-44 23 445, the reaction is carried out in boiling methanol (64.5° C.) and the isolation of the nifedipine is carried out at approximately 0° C.

Through the use of the catalyst the process of DE 44 23 445 admittedly does lead to a shortening of the reaction times, but the products obtained also show a purity which is inadequate for use as a pharmaceutical active compound. Thus in the products obtained, in addition to the abovementioned valence isomer (II), pyrimidine derivatives and lactones occur which necessitate a pure crystallization which leads to a total yield of below about 80% of theory.

The inventors therefore undertook intensive investigations with the aim of making available a process for the preparation of nifedipine in high purity and with high yields and at the same time with a short reaction time, which allows the nifedipine obtained to be used immediately as an active compound in medicaments without further purification operations. In the course of these, they discovered that the catalyst used in the process of DE 44 23 445, in addition to the desired acceleration of the reaction to give nifedipine, also leads to the increased formation of by-products. Additionally, they surprisingly discovered that when carrying out the reaction in the absence of a catalyst at temperatures above the boiling point of the $(C_1-C_3)$alkanol, in particular of methanol, i.e. at elevated pressure, the formation of the desired product, nifedipine, is accelerated, whereas, however, the formation of the by-products is not accelerated, and the nifedipine is obtained in such pure form after a short reaction time that it can be isolated without further purification and used as an active compound in pharmaceutical preparations. The present invention was completed on the basis of these findings.

The present invention makes available a process for the preparation of nifedipine, which comprises the reaction of methyl 2-(2-nitrobenzylidene)acetoacetate and methyl 3-aminocrotonate in at least one $(C_1-C_3)$alkanol as solvent, and is characterized in that the reaction is carried out under pressure at a temperature between 70 and 110° C. Carrying out the reaction under pressure means a pressure which is above atmospheric pressure, i.e. above approximately 1 bar.

The process for the preparation of nifedipine of the invention is carried out in the absence of catalytic amounts of a lower carboxylic acid, preferably in the absence of any catalyst.

The process for the preparation of nifedipine of the invention is carried out in at least one $(C_1-C_3)$alkanol as solvent. The ($C_1$–$C_3$)-alkanols include methanol, ethanol, n- and iso-propanol, and mixtures thereof. Since the reaction is carried out at above atmospheric pressure, the temperature ranges of the reaction for the ($C_1$–$C_3$)alkanols follow accordingly.

Preferably, the reaction is carried out in methanol at temperatures between 75 and 95° C., particularly preferably at approximately 85° C. Since the boiling point of the solvent (methanol) at normal pressure is approximately 65° C., the reaction must be carried out at elevated pressure above atmospheric pressure. In this case, the temperature range from 70 to 100° C. corresponds approximately to a pressure range of approximately 1 bar to approximately 3 bar.

The process for the preparation of nifedipine of the invention is preferably carried out in such a way that the methyl 2-(2-nitrobenzylidene)acetoacetate and the methyl 3-aminocrotonate are reacted in a molar ratio of methyl 2-(2-nitrobenzylidene) acetoacetate/methyl 3-aminocrotonate of 1 to 1.5.

The process for the preparation of nifedipine of the invention is preferably carried out such that at the start of the reaction the concentration of the methyl 2-(2-nitrobenzylidene)acetoacetate is up to 55% by weight of the reaction mass.

The process for the preparation of nifedipine of the invention is preferably carried out such that the reaction time of the reaction of the methyl 2-(2-nitrobenzylidene) acetoacetate and of the methyl 3-aminocrotonate is between 2 and 20 hours.

In a particularly preferred embodiment of the invention, the nifedipine formed in the reaction is isolated at a temperature which is above room temperature (25° C.), preferably between 30° C. and 50° C., particularly preferably between 35° C. and 45° C. and very particularly preferably at approximately 40° C.

The nifedipine formed by the process for the preparation of nifedipine of the invention contains less than 1000 ppm, preferably less than 700 ppm, of by-products.

The invention further relates to the use of the nifedipine prepared by the process of the invention for the production of a medicament.

It is the preferred embodiment here to use the nifedipine prepared by the process of the invention without further purification for the production of a medicament.

The reaction mixture of the invention forms a clear solution above 90° C., such that under these conditions a filtration customary in the synthesis of pharmaceutical active compounds can be carried out, which represents a further advantage of working at elevated pressure in the temperature range indicated.

Under elevated pressure in the temperature window indicated, the process of the invention leads unexpectedly to a significant reduction in the reaction time. The reaction is complete even after 8 to 12, preferably 8 to 10, hours. It was completely surprising here that at the same time the valence isomer (II), which occurs as a by-product in the processes described in the prior art, can also no longer be detected.

Furthermore, it was surprisingly found that after isolation of the crystalline (I) from the suspension at temperatures above 25° C. the nifedipine is obtained in a purity which fully meets the demands which are made of a pharmaceutical active compound. The absence of a purification operation in the preparation of the nifedipine according to the process of the invention is an important economical factor compared with the processes described in the prior art. In particular, it is to be taken into consideration here that the product of DE-A-44 23 445 is obtained in a lower total yield such that the process of the invention is more economical both due to the absence of the purification operation and the higher total yield.

According to the process of the invention, nifedipine is obtained with a yield of 85% of theory in a quality which can be obtained according to the previously known synthesis processes only by an additional pure crystallization with the yield losses occurring in this pure crystallization.

WORKING EXAMPLE 1185 g (4.76 mol) of methyl 2-(2-nitrobenzylidene) acetoacetate are heated to 85° C. in a closed stirring vessel together with 600 g (5.22 mol) of methyl 3-aminocrotonate in 1900 ml of methanol and stirred for 10 hours at 85° C. The mixture is then cooled to 40° C. The crystallizate is filtered off with suction and washed with methanol and water. After drying in vacuo, 1400 g (=85% of theory) of nifedipine are obtained.

What is claimed is:

1. Process for the preparation of nifedipine, comprising:

mixing methyl 2-(2-nitrobenzylidene) acetoacetate and methyl 3-aminocrotonate in at least one ($C_1$–$C_3$) alkanol solvent in the absence of a catalyst to obtain a reaction mixture of methyl 2-(2-nitrobenzylidene) acetoacetate, methyl 3-aminocrotonate and solvent;

heating said reaction mixture in a closed container at a temperature between 70° C. and 110° C. so as to react said methyl 2-(2-nitrobenzylidene) acetoacetate with said methyl 3-aminocrotonate; and isolating the nifedipine formed by the reaction of methyl 2-(2-nitrobenzylidene) acetoacetate and methyl 3-aminocrotonate at a temperature between 30° C. and 50° C.

2. Process for the preparation of nifedipine according to claim 1, wherein said solvent is methanol.

3. Process for the preparation of nifedipine according to claim 1, wherein said temperature is between 75° C. and 95° C.

4. Process for the preparation of nifedipine according to claim 1, wherein a molar ratio of methyl 2-(2-nitrobenzylidene) acetoacetate/methyl 3-aminocrotonate is 1/1.5.

5. Process for the preparation of nifedipine according to claim 1, wherein said reaction mixture is heated between 2 and 20 hours.

6. Process for the preparation of nifedipine according to claim 1, wherein said nifedipine formed by the reaction contains less than 1000 ppm of by-products.

* * * * *